(12) United States Patent
Kulmala et al.

(10) Patent No.: US 9,176,092 B2
(45) Date of Patent: Nov. 3, 2015

(54) INTEGRATED CARBON ELECTRODE CHIPS FOR THE ELECTRIC EXCITATION OF LANTHANIDE CHELATES, AND ANALYTICAL METHODS USING THESE CHIPS

(75) Inventors: Sakari Kulmala, Kirkkonummi (FI); Timo Kalevi Korpela, Turku (FI); Jarkko Uolevi Eskola, Turku (FI); Johanna Suomi, Helsinki (FI); Markus Hakansson, Epoo (FI); Teppo Tapani Laaksonen, Turku (FI)

(73) Assignee: LABMASTER OY, Turku, FL (US)

( * ) Notice: Subject to any disclaimer, the term of this patent is extended or adjusted under 35 U.S.C. 154(b) by 307 days.

(21) Appl. No.: 13/703,393

(22) PCT Filed: Jun. 10, 2011

(86) PCT No.: PCT/FI2011/000032
§ 371 (c)(1),
(2), (4) Date: Jan. 17, 2013

(87) PCT Pub. No.: WO2011/154590
PCT Pub. Date: Dec. 15, 2011

(65) Prior Publication Data
US 2013/0206610 A1    Aug. 15, 2013

(30) Foreign Application Priority Data

Jun. 11, 2010 (FI) .................................... 20100246
Jun. 15, 2010 (FI) .................................... 20100251
Jun. 16, 2010 (FI) .................................... 20100253

(51) Int. Cl.
*G01N 27/327* (2006.01)
*G01N 21/66* (2006.01)

(52) U.S. Cl.
CPC ............ *G01N 27/3276* (2013.01); *G01N 21/66* (2013.01)

(58) Field of Classification Search
CPC ..................................................... G01N 21/76
USPC .................. 204/400, 403; 428/432; 436/518; 422/52
See application file for complete search history.

(56) References Cited

U.S. PATENT DOCUMENTS

| 5,308,754 | A | 5/1994 | Kankare et al. |
| 6,251,690 | B1 * | 6/2001 | Kulmala et al. ............... 436/518 |
| 7,005,108 | B2 | 2/2006 | Ala-Kleme et al. |
| 7,494,820 | B2 | 2/2009 | Yang et al. |
| 7,560,237 | B2 * | 7/2009 | O'Connor et al. ............. 435/7.1 |

(Continued)

FOREIGN PATENT DOCUMENTS

| JP | 2009-204375 | * 10/2009 | ........... G01N 27/327 |
| JP | 2009204375 A | 10/2009 | |
| WO | WO 9641177 A1 | 12/1996 | |
| WO | WO 2009126249 A1 | 10/2009 | |

OTHER PUBLICATIONS

Bard and Faulkner (Electrochemical Methods, John Wiley and Sons, Copyright 1980.*

(Continued)

*Primary Examiner* — Luan Van
*Assistant Examiner* — Steven Rosenwald
(74) *Attorney, Agent, or Firm* — Gearheart Law LLC (57) ABSTRACT

Electrochemiluminescent technique and device suitable for cheap analytical and diagnostic applications, with electrodes manufactured from carbon paste and terbium chelates as labeling compounds.

7 Claims, 4 Drawing Sheets

(56) References Cited

U.S. PATENT DOCUMENTS

2004/0022677 A1    2/2004    Wohlstadter et al.
2004/0189311 A1*   9/2004    Glezer et al. ................. 324/444
2007/0034529 A1*   2/2007    Bard et al. .................... 205/775

OTHER PUBLICATIONS

Kulmala et al. (Anal. Chim. Acta, 367, 1998, 17-31.*

PCT/FI2011/000032—International Search Report; Oct. 5, 2011 (5 pgs).

Fredrick, S.J., et al; Use of microelectrodes for electrochemiluminescent detection in microfluidic devices; http://www.future-science.com/doi/abs/10.4155/bio.09.1((Abstract).

Wu, A-H, et al; Hot Elexctron Induced Cathodic Electrochemiluminescence at Disposable Screen Printed Carbon Electrodes; http://onlinelibrary.wiley.com/doi/10.1002/elan.201000233/abstract.

* cited by examiner

SEQUENCE LISTING

<160> NUMBER OF SEQ ID NOS: 2

<210> SEQ ID NO 1
<211> LENGTH: 26
<212> TYPE: DNA
<213> ORGANISM: artificial sequence
<220> FEATURE:
<223> OTHER INFORMATION: chemically synthesized

<400> SEQUENCE: 1
ttagccgcat tcagggggcg aaaaaa                                         26

<210> SEQ ID NO 2
<211> LENGTH: 21
<212> TYPE: DNA
<213> ORGANISM: artificial sequence
<220> FEATURE:
<223> OTHER INFORMATION: chemically synthesized

<400> SEQUENCE: 2
gaaacacgga cacccaaagt a                                             21

INTEGRATED CARBON ELECTRODE CHIPS FOR THE ELECTRIC EXCITATION OF LANTHANIDE CHELATES, AND ANALYTICAL METHODS USING THESE CHIPS

PRIORITY

This application is a national entry of PCT/FI2011/000032 filed on Jun. 10, 2011 which claims priority of FI20100246 filed on Jun. 11, 2010, FI20100251 field on Jun. 15, 2010 and FI20100253 filed on Jun. 16, 2010, all of which are fully incorporated herein by reference.

SEQUENCE LISTING

This application contains sequence data provided on a computer readable diskette and as a paper version. The paper version of the sequence data is identical to the data provided on the diskette.

FIELD OF THE INVENTION

The invention relates to analysis methods and instruments suitable for electrochemiluminescent detection. The invention specifically applies to the quantitative fast diagnostics of decentralized analyses when especially cheap electrode materials, cells, single-use diagnostic chips and cassettes are needed.

BACKGROUND OF THE INVENTION

There has been great commercial demand for fast, sensitive and quantitative technologies for diagnostical purposes for quite some time. These technologies are suited to be used in a very wide market area comprising of health care, research, agriculture, environmental care, veterinary care and some areas of industrial production. The increased sensitivity, high throughput, ease of use, ruggedness or lower cost per test are factors that may open new areas of use if they can be realized with these diagnostic technologies.

Certain diagnostic technologies can reach high sensitivity but at a high cost. Other methods might be commercially competitive, but they cannot be applied widely enough to serve different market areas. A technology combining the demand for high sensitivity with commercial feasibility and wide applicability will in the future have an important position and great possibilities at the diagnostic market.

At the moment diagnostic applications use several different analysis methods, e.g., radioactive labeling, enzyme linked immunoassay, colorimetric determinations, and determinations on the basis of fluorescence, chemiluminescence, and anodic or hot electron induced electrochemiluminescence (ECL). Hot electron-induced electrogenerated chemiluminescence (HECL) has been described in detail in the U.S. Pat. No. 6,251,690, Kulmala S., et al. Each of these techniques has a characteristic combination of sensitivity levels, ease of use, ruggedness, speed and operation costs, which determines the marketability. The differences in these properties come from the physical limitations of the methods. For example, the disadvantage of many applications of radioactive labeling is the weakening of the label with time as a result of radioactive fission as well as the extra costs of radioactive waste both from a safety point of view and from an environmental point of view. Application of many sensitive techniques in decentralized diagnostics is limited by the extreme complexity of the tests and the instrumentation, so that only experts can do the measurements. The complexicity of the measurement is also usually in direct relation to the cost of the instrumentation and/or the test. As an example can be mentioned, among others, anodic electrochemiluminescence (ECL), which has become a commercially popular method of detection. The instrumentations based on anodic ECL are laboratory robots with intricate features of use, so that expert knowledge is needed to use them; in addition, the measurement process includes repeated complex washing and preparation steps. All of the above mentioned things are factors increasing the cost of measurements, increasing the amount of waste and making it impossible to employ the analysis method for the practical needs of decentralized analysis.

Commercially important measurement techniques are based on the identification and the measurement of the analytes in mixtures with use of so-called labeling compounds. In measurements based on properties of biological molecules, such as immunoassays, the analyte to be measured (X) can be selectively attached from a mixture of different molecules to an antibody on a solid phase, and the attached molecules can be measured with the help of another, also compound (X) specific antibody, which has been marked, i.e., labeled with a suitable labeling compound. Examples of labeling compounds include, but are not limited to, radioactive isotopes, enzymes, light-absorbing molecules, fluorescent or phosphorescent molecules, certain metal chelates etc. The labels are attached to the antibody by means of a chemical bond. The purified compound (X) can also be labeled and used to determine the unlabeled (X) in an unknown sample by a competitive reaction. The measuring techniques of DNA and RNA are also based on selective bioaffinity and they can therefore be measured in an analogous manner. Several other chemical and biochemical analyses can be performed in this way. These days it is increasingly desirable to measure simultaneously several parameters from the sample to lower the costs and/or to increase the measurement accuracy. One possibility to achieve simultaneous measurement is to use labels that are luminescent (fluorescent or phosphorescent) at different wavelengths or have different lifetimes. Different methods and strategies of measurement, which can be used in immunodiagnostics, have been described in the book The Immunoassay Handbook, Edited by David Wild, Stockton Press Ltd., New York, 1994, pages 1-618. Naturally it is possible to measure the labeling compounds in solutions also "as is", i.e., analyzing only the compounds when they are not used as labels.

It is previously known that organic compounds and metal chelates, which are suitable to be used as labeling compounds in analyses, can be excited with light or electrochemically so that labeling-compound specific luminescence is produced. Photoluminescence or electrochemiluminescence based techniques are usually very sensitive and well suited to excitation of labeling compounds. However, since the measured concentrations are very low, case-specific difficulties arise. The use of fluorescence can be complicated by, among others, Tyndall, Rayleigh and Raman scatterings. When measuring biological samples there appears after the excitation pulse almost without fail strong but short-lived background fluorescence. In liquid phase, phosphorescence is mainly usable only when lanthanide ions are used with specially synthesized organic molecule chelates. The problem for these techniques based on the long-lived photoluminescence of labeling compounds is the complexity and the cost of the instrumentation.

Generally the special advantages of ECL are the low cost of the electric excitation and the more simple structure (in comparison with photoluminescence), in which complex excitation optics is not needed. In addition many of the problems of photoluminescence, as described above, are avoided. The usual, so-called anodic electrochemiluminescence, in which inert metal electrodes are used, is possible to perform with organic luminophore labels with relatively simple equipment in nonaqueous solvents. However, bioaffinity assays, which are the main commercial point of interest, for the most part work only in aqueous solutions. The samples for bioaffinity assays are nearly always aqueous solutions, and thus the measuring technique for the labels has to work in water or at the very least in a micellar aqueous solution. In addition, only certain transition metal chelates can function as ECL labels in anodic ECL in aqueous or micellar aqueous solutions.

Thus far the most important commercially used anodic ECL application in analytical chemistry is a technique utilizing the derivatives of $Ru(bpy)_3^{2+}$ chelate as labels and detecting the labels in a micellar water solution. Micellar solutions are always sensitive to various disturbing factors as a result of the uncontrolled complexity of micellar equilibria.

Hot electron-induced ECL, which is not dependent on micelles, has therefore several significant advantages in comparison to anodic ECL. Therefore the examples of this invention mainly draw upon cathodic ECL. The anodic method is also usable in both immunoassays and in DNA hybridization assays (Blackburn, G., et al., 1991, Clin. Chem. 37: 1534-1539; Kenten, J., et al. 1992, Clin. Chem. 33: 873-879). This method is currently in commercial use by Roche Diagnostics. A laboratory robot moves magnetic particles with which the label for the quantitative measurement of the analyte is transferred onto a golden continuous-use working electrode to perform immunoassays and DNA or RNA probe applications (Massey, Richard J., et al. U.S. Pat. No. 5,746,974; Leland, Jonathan K., et al. U.S. Pat. No. 5,705,402). The repeatable handling of magnetic latex particles is in many ways difficult, which is why this technique is usable only with expensive laboratory robots (e.g. Elecsys 1010 and 2010) with complex and exact liquid handling device. In addition the continuous-use massive golden working electrode demands a lengthy cleaning and pretreatment between each analysis (Elecsys Service Manual, p. 70).

Using microparticles in electroluminescence is not necessarily optimal, because as U.S. Pat. No. 5,705,402 shows, the excitation of the label substance occurs on the surface of the microparticle in contact with the gold electrode. Even though microparticles are tiny (diameter e.g. 2800 nm), only a very small part of the surface of the spherical particle can be in contact with the electrode. Consequently only a small part of the labeling substance carried by the microparticle is available for excitation. The operating efficiency is further decreased by the poor optical transparency of the magnetic material containing latex particles, since only a part of the photons can be seen at the detector at the opposite direction from the (optically non-transparent) working electrode. This direction is one where the detector is generally found in traditional analysers.

Usual anodic ECL based on traditional electrochemistry requires the use of inert metals (e.g., platinum or gold) or carbon as working electrodes. The use of these electrode materials is however limited by their narrow potential window as a result of water breaking down (oxygen produced at the anode and hydrogen at the cathode). Luminophores suitable for use as ECL labels cannot therefore be electrically excited by common means on these traditional inert electrodes, as due to the limited potential window one cannot reach high enough anodic and cathodic potentials needed for excitation reactions. This is also why anodic ECL cannot achieve the simultaneous excitation and/or time-resolved detection of several different labels, which is necessary for multiparameter assays. Anodic ECL is only suited to the needs of very large centralized laboratories. As a result of the extreme complexity and high cost of the measuring device the anodic device and technique are not suited in their previously known form to be used in the market area of decentralized analyses, e.g., during a doctors' appointment, at small health clinics, or at the patient's home.

A special disadvantage for both anodic ECL and HECL in bioaffinity assays, in addition to the problems discussed above, is the long incubation time needed to let the reactive molecules reach kinetic equilibrium, which is necessary to optimize the accuracy of the analysis. This problem can be solved fairly efficiently with the aid of porous disk devices (US 2009178924 (A1), Ala-Kleme, T. et al.). The problem with these devices is that thus far they have only included a working electrode, and the counter electrode has been inside the continuous-use cell of the electrochemiluminometer. The careful washing of the cell is imperative and sometimes very difficult, and especially the removal of anodic films forming on the counter electrode is difficult and time-consuming. As an alternative, the counter electrode would have to be placed, with difficulty, in the measuring cassette near the working electrode but so that it would not overmuch impede the light from reaching the electrode.

Hot electron electrochemistry has been utilized on flat surfaces with an insulator-covered silicon electrode or an insulator-covered aluminium electrode as the working electrode (FI 20100246, Kulmala, S., et al.) and with a conductor as the anode. The problem of hot electron electrochemistry is that there is no known electrode type that could achieve the flat plane integrated anode/cathode system with the same electrode material and reach at all as good results as with oxide-covered silicon or aluminium cathodes. The problem of silicon and aluminium is that the flat plane integrated cathode/anode chips made of these materials cannot be exploited, because labels can only be excited through a few of the first excitation pulses. After that the very fast anodic oxide layer formation soon totally prevents the current passing through the cell, and also during the formation of the oxide layer occurs a very high intensity solid state electroluminescence (also known by the old name of galvanoluminescence). Galvanoluminescence, unfortunately, also contains long-lived luminescence components, and thus time-resolved electrochemiluminescence measurement cannot be used with lanthanide chelate labels. By protecting the surface of the aluminium or silicon cathode/anode chip with an organic polymer one can diminish the problem, but it appears it is impossible to find such an electrode material that could achieve successful use of flat plane cathode/anode chips with excitation of labeling compounds in bioaffinity assays.

As we endeavoured to make a cathode/anode chip, on which the anode part of aluminium electrode glass-based chip was supposed to be covered with carbon paste to prevent anodic oxidation, by mishap both the anode and the cathode parts were covered with the carbon paste. Since the chips had been made, they were tested in measurements, and surprisingly Tb(III) chelate gave light with high amplitude electric pulses. We assumed that this was due to hot electron electrochemistry, even though tunnel emission with carbon electrodes and other conductors is not possible. For comparison we tried to excite also organic fluorophores (8-hydroxy quinolone and 7-amino-4-methyl coumarine), but none of which gave measurable ECL with the carbon electrodes. Thus it is probable that we have found a previously unknown carbon electrode related phenomenon that is suited to electric excitation or terbium chelates on a pair of carbon electrodes.

Fullerenes, carbon nanotubes and similar foundations of current new carbon technologies have been found only recently, and carbon chemistry might have a lot of still unknown and unstudied parts. The excitation we described may somehow be caused by the electrode surface being in direct contact with the terbium ions, instead of the excitation occurring via the ligand. One can also speculate that the gases forming on the electrode surface (hydrogen and oxygen, especially in their atomic forms) have a significant part in the reaction mechanisms. In any case the electrochemiluminescence presented in this invention can be efficiently used in bioaffinity assays even if the reaction mechanisms are still unclear.

According to this invention one can produce electrode/electrode chips (EE chips) to replace cathode/anode chips. In EE chips it does not matter which of the two electrodes on the chip is used as the cathode and which as the anode. Production of carbon paste electrodes by printing methods is probably the cheapest possible production technique for electrodes, as a result of which this innovation is a groundbreaking one from the point of view of single-use electrochemiluminescence-based diagnostic chips and cassettes. Thus a very competitive electrochemiluminescence technique (as compared with HECL-based techniques) can be accomplished using the sort of EE chips described in this invention, which are significantly cheaper than the ones used in HECL. The methods and equipments through which the above is possible are introduced in the patent requirements 1-10.

It is also noteworthy that such a carbon electrode couple as described in this invention can be produced directly on one half of a polymer cassette, after which the said half in itself is a larger than usual EE chip. On top of this half can be integrated fluidistic operations as well as operations to take, add and filter samples as well as to add reagents. This half needs not be optically transparent. The half without the carbon electrode is by preference totally optically transparent, but it can also contain only optically transparent window part. This window formation can also, if needed, function as an optical filter if the materials are chosen accordingly.

FIGURE CAPTIONS

FIG. 1. A simple EE chip. The base is a 19 mm×10 mm glass or plastic chip (1) on top of which the electrodes (2) and (3) were attached with double-sided tape, painted with a brush or printed. On top of the dried electrodes was glued a ring (4) made of adhesive plastic sheets by perforation; the ring was glued on the chip with the help of its own adhesive glue so that a 7 mm inner diameter cell area (5) was formed. 80 to 150 µL of the sample or other solution could be pipetted in the cell.

FIG. 5. PDMS chip connected to an EE chip. (1) Base part, typically made of polymer, paper, cardboard or glass, or any combination thereof; (2) and (3) identical carbon electrodes, which can optionally be coated differently; (4) PDMS chip with incubation chamber and measurement chamber (5) on the lower surface and an open chamber reaching through the chip for sample input and reagent addition (6), microchannels (7) leading to the incubation area, and air removal channels (8). The PDMS chip and the EE chip were pressed together with small clamps. The cassette could equally well have been glued together, but to prevent possible blocking of the microchannels clamping junction was used. Instead of clamps it would also have been possible to use a plastic frame to keep the chips tightly together.

DETAILED DESCRIPTION OF THE INVENTION

This invention shows how simple and cheap equipment can be used for different analyses as efficiently as with previously described complicated instrumentation, when the immunoassay or DNA hybridization are performed on a single-use EE chip or using also a porous layer on top of the EE chip. By this means both the measurement device and the measuring cell are cheap enough for the needs of decentralized analysis.

This invention describes different ways of producing EE cells on top of different cheap materials. These materials include, among others, different sorts of plastic, polymers, paper, paper with different types of coatings, and cardboard. Materials like these are easy to couple to a micro analysis system or a cassette, which takes care of all other functions needed for the analysis. In mass production when one strives to manufacture high quality goods at low prices, printing methods are a very good option as a production method. Electrodes described in this invention are extremely well suited to be manufactured by methods of printing technology, which gives a significant competitive advantage on the market.

It is previously known that carbon electrodes can be used as single-use anodes in context of electrochemiluminescence of ruthenium (FI981568 (A), Kulmala, S., et al.), but single carbon anodes cannot be used to excite terbium chelates. An expert in the area could not imagine that by replacing the platinum electrode in a carbon-platinum electrode pair with a carbon electrode one could achieve a special electrode system with special behavior at least when the electrodes are level and near each other (so far we do not have experience of different geometries). We are not entirely certain yet whether the light is produced when the electrodes function anodically or cathodically or if the reaction is a result of the combined effect of intermediates produced at different polarities. From the experimental results it appears that the main part of the light at least is produced at the cathode.

This invention presents a significant enhancement on the instrumentation and methods meant for the decentralized analysis market and makes cheap, quantitative and fast testing possible. The above is achieved by using EE cells either in their simplest form, fitted with a hydrophobic ring defining the cell area, or as an integrated element in a more complex analysis cassette.

The objective of this invention is a method and a device to excite labels in bioaffinity assays either directly from the surface of the EE chips or with the help of porous layers (porous membranes) in the EE chip device. The method can be used in immunochemical and DNA probe quick assays. It may also be possible that in time some other labels than terbium chelates can be excited with EE chips and methods described in this invention.

The invention consists of a device, where the main part is an EE chip. The surface of the electrodes of the EE chip can be coated by known means with antibodies or DNA and label molecules attached to the coating can be excited by electric pulses. According to the invention the electrode part (or the surface of the optional porous layer that comes in contact with the electrode part) can be coated with Langmuir-Blodgett films or other easily made films that create special advantages.

Sometimes great advantages are reached when using porous membranes in bioaffinity assays. With help of the porous layer the sample is uniformly spread on the antibody-coated electrode complex. The porous layers also appear to function as homogenic compensators of liquid flow and to prevent in microfluidistc systems bubble formation, temperature diffusion and surface forces as well as to eliminate problems caused by these e.g., in microfluidistic micro-flow cells or microlayered cells.

Films (porous layers, aka porous membranes) sometimes used in the invention on electrode surfaces, are characterized by their microporosity and their less than 100 μm thickness. These kinds of materials are commercially available from many sources, such as Millipore, MSI, Sartorius, Pall, Sigma and DuPont. The membranes can be either isotropic or anisotropic. The manufacturing techniques of the films are varied and may contain pressing or stretching, the pores may be formed either chemically or physically, and in anisotropic films, by phase transfer. Suitable materials include PTFE, polyvinylidene fluoride, polycarbonate, polysulphone, nylon and cellulose esthers. These are available from commercial sources with different pore sizes and thicknesses and with different physicochemical properties. Fibrous materials that can be used include fiber filters, filtration paper, filtration cloth, etc.

For manufacturing reasons the EE chips are best kept dry. The devices are then set to working order by adding liquid sample or buffer solution on the EE chips or on the porous layer in the chips. Thus conditions suitable for bioaffinity reactions are achieved either directly on the electrodes or between the membrane and the electrode.

There are plenty of different, alternative options for the EE chips this invention describes. The basic choice is to directly use a sufficiently conductive carbon paste to manufacture the electrodes on the chip, which is typically either plastic, paper or glass chip or strip, and most typically the manufacturing is done by printing technologies. Should the conductance of the carbon paste be insufficient, one can make a highly conductive layer below the carbon paste from e.g. silver ink or thin metal layer, which is then extensively covered with the carbon paste. Thus already relatively low voltages are enough to produce ECL as the potential drop does not happen in a long distance inside the resistive carbon paste film.

EE chips are usually attached to be part of a diagnostic cassette by various different techniques and by utilizing the best properties of different materials. The aim is to prepare the parts of the cassette, usually made of polymers, e.g., channels and cells, so that after the addition of the reagents by dry chemistry they allow all the necessary functions of the diagnostic measurement, typically so that the single-use cassette is never opened during use or afterwards.

In the following the invention is further illustrated by diagrams and non-limiting examples and figures related to the examples.

EXAMPLE 1

Figure 1:
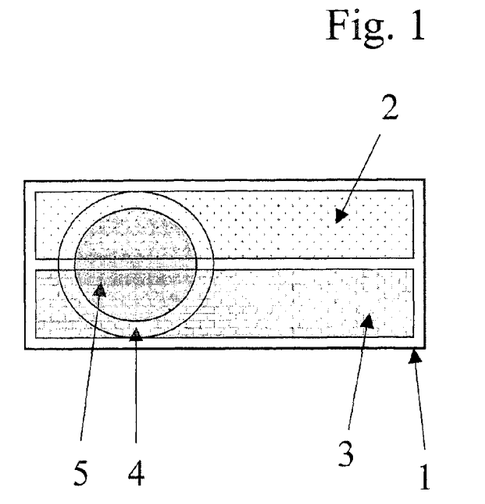
Figure 2:
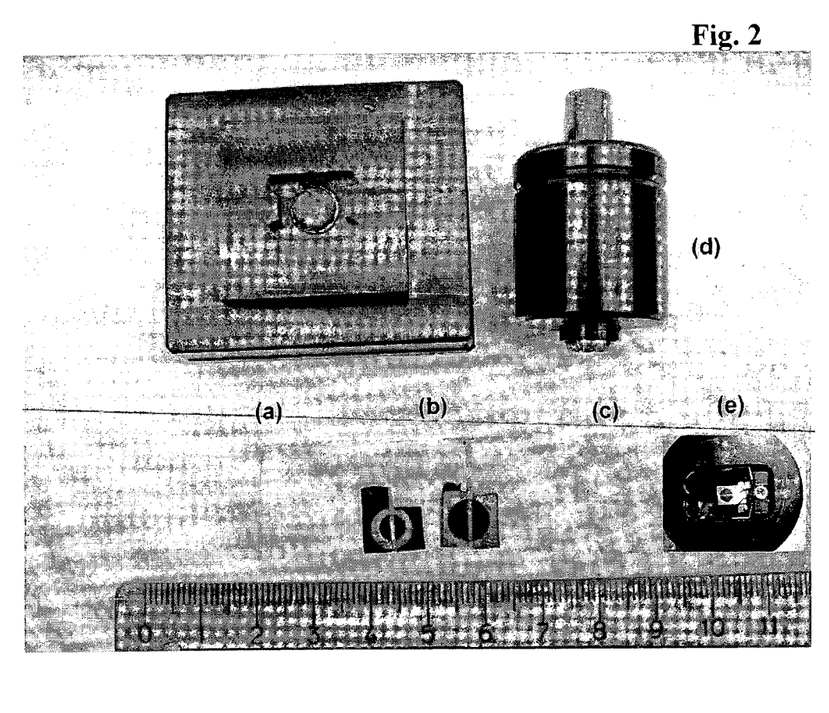
FIG. 2. Plastic cell bases (a); EE chip where carbon electrodes have been made on top of aluminium or a silver ink layer so that the electric contact surfaces of the electrodes have been left free of carbon paste (b); Tape with protective film at bottom from the perforator (c); Perforation tool for square tapes and self adhesive labels (d); EE chip in place in the measurement cell awaiting sample pipetting.

Manufacturing EE Chip Electrodes so that in the Cell Area the Electrode Material Consists Only of Carbon Paste An electrode pair, shown in FIG. 1, was painted from carbon paste (Creative Materials 110-04 Carbon Ink, Tyngsboro, Mass., USA) on top of a 10×19 mm plastic chip using a template. A 0.2 mm high and 0.5 mm wide shoulder had been left in the middle of the chip when it was manufactured by milling, and this shoulder was used as a resistor between the electrodes (FIG. 2 (b)). After the carbon paste had dried an extra layer was painted with silver ink (Bison electro G-22, Bison Inc, Netherlands) and this silver layer nearly reached the cell area (FIG. 2). The cell area was formed by attaching a perforated piece of Teflon tape (Irpola Oy, Turku, Finland) or an ordinary perforated tape piece (a square one, unlike the round piece shown in FIG. 1, with a 7 mm or 8 mm i.d. hole in the middle of the piece) to the left end of the electrode as shown in FIG. 1. Both Tb-2,6-bis[N,N-bis(carboxymethyl)aminomethyl]-4-benzoylphenol chelate and Tb(III)-$N^1$-4-isothiocyanatobenzyl)diethylenetriamine-$N^1,N^2,N^3,N^3$ tetraacetate chelate could be excited and measured with time resolution in this cell. A significantly higher intensity is, however, reached with EE chips of Example 2, with which however the corresponding chelates of other lanthanide ions gave significantly lower intensities than terbium.

EXAMPLE 2

Manufacturing EE Chip from Silver Ink Covered with Carbon Paste

An electrode pair, shown in FIG. 1, was painted from silver ink (Bison electro G-22, Bison Inc, Netherlands) on top of a 10×19 mm plastic chip using a template. An 0.2 mm high and 0.5 mm wide shoulder had been left in the middle of the chip when it was manufactured by milling, and this shoulder was used as a resistor between the electrodes. After the silver ink had dried (5 h) a covering layer of carbon paste (Creative Materials 110-04 Carbon Ink, Tyngsboro, Mass., USA) was added on top of it and left to dry at room temperature overnight. The cell area was formed by attaching a perforated piece of Teflon tape (Irpola Oy, Turku, Finland) or an ordinary perforated tape piece to the left end of the electrode as shown in FIG. 1. The calibration curve of Tb-2,6-bis[N,N-bis(carboxymethyl)aminomethyl]-4-benzoylphenol chelate is presented in FIG. 3 (a), open circles. The measuring instrument consisted of a Stanford Research SR400 photon counter, a coulostatic pulse generator and a black plastic electrode chamber with a Perkin Elmer channel photomultiplier tube module attached. The parameters in the measurements were: Pulsed voltage −67V, pulse charge 30 μC/pulse, pulse frequency 20 Hz. ECL intensity was integrated over 1000 excitation cycles, delay time 0.05 ms, measuring window 6.0 ms. 0.05 M sodium tetraborate buffer, pH 9.2, was used.

EXAMPLE 3

Manufacturing EE Chip on Paper from Carbon Paste

At first baking paper (greaseproof paper) was coated with silver ink (Bison electro G-22, Bison Inc, Netherlands), after which a layer of carbon paste (Creative Materials 110-04 Carbon Ink, Tyngsboro, Mass., USA) was coated on top of the silver. Templates were used in the coating to imitate silkscreen printing. After the carbon paste had dried at room temperature for 2 h, strips fit to be used on the bases in FIG. 2 were cut from the paper. The edge of the paper by the shoulder of the base was painted with carbon paste so that silver would not be in direct contact with the electrolyte solutions. Finally the paper was attached to the plastic base by double-sided tape (3M) and the tape rings forming the cell area were attached to the chip.

Figure 3:
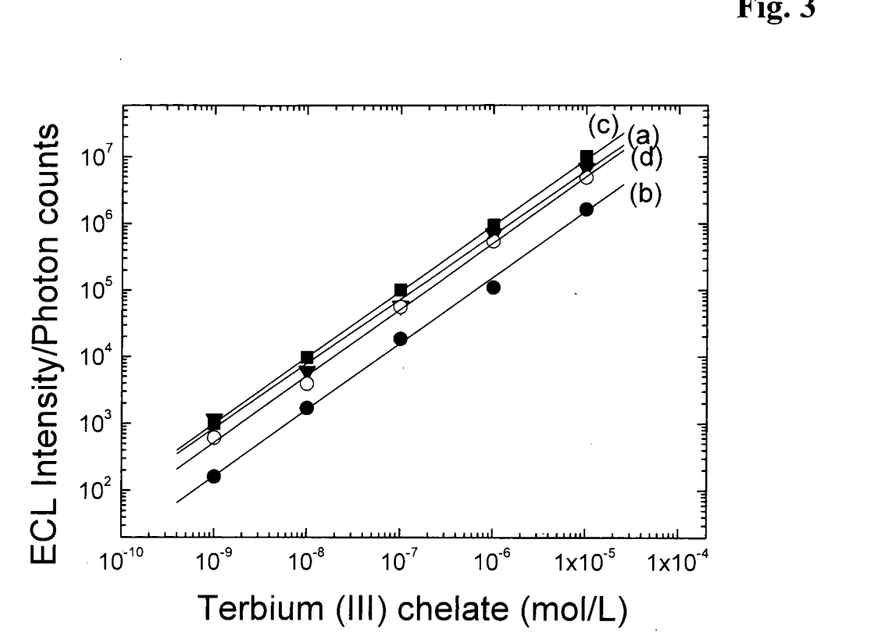
FIG. 3. Tb(III) chelate calibration curves on differently manufactured carbon paste electrodes. (a) Electrodes of Example 2. (b) Electrodes of Example 3. (c) Electrodes of Example 4, and (d) Electrodes of Example 5.

The calibration curve of Tb-2,6-bis[N,N-bis(carboxymethyl)aminomethyl]-4-benzoylphenol chelate is presented in FIG. 3 (b), closed circles. The measurement parameters were the same as in Example 2.

EXAMPLE 4

Manufacturing EE Chip from Metal Foil Strips Coated with Carbon Paste

At first the electrode pair was made by gluing aluminium foil strips on top of a 10×19 mm plastic chip. An 0.2 mm high (or optionally 0.3 mm or 0.4 mm high) and 0.5 mm wide shoulder was left in milling in the middle of the chip to function as resistor between the electrodes (FIG. 1). The aluminium foil strips were coated with carbon paste (Creative Materials 110-04 Carbon Ink, Tyngsboro, Mass., USA) so that at the right edge the contact areas of spring loaded studs/pins (which attach the chip to the pulse generator of the device) were left uncovered. The cell area was formed by attaching either a perforated piece of Teflon tape (Irpola Oy, Turku, Finland) or an ordinary perforated piece of tape at the left end of the electrode according to FIG. 1. The calibration curve of Tb-2,6-bis[N,N-bis(carboxymethyl)aminomethyl]-4-benzoylphenol chelate is presented in FIG. 3 (c), closed squares. Similar electrodes can also be made by starting from aluminium plates produced by vapor deposition, as in Example 8. The measurement parameters were the same as in Example 2.

EXAMPLE 5

Manufacturing EE Chip from Commercially Available Metal Stickers Covered with Carbon Paste At first the electrode couple was manufactured by gluing copper folio stickers (Screen House, Turku, Finland) with their own adhesive on top of the 10×19 mm plastic chip. An 0.3 mm high and 0.5 mm wide shoulder was left during milling in the middle of the strip to function as a resistor between the electrodes (FIG. 1). The copper folio strips were coated with carbon paste (Creative Materials 110-04 Carbon Ink, Tyngsboro, Mass., USA) so that the contact areas of spring loaded pins to the pulse generator at the right edge of the strip were left unpainted. The cell area was formed by attaching either a perforated piece of Teflon tape (Irpola Oy, Turku, Finland) or an ordinary perforated piece of tape at the left end of the electrode according to FIG. 1. The calibration curve of Tb-2,6-bis[N,N-bis(carboxymethyl)aminomethyl]-4-benzoylphenol chelate is presented in FIG. 3 (d), closed circles. Similar electrodes can also be made by starting from aluminium plates produced by vapor deposition, as in Example 8. The measurement parameters were the same as in Example 2.

EXAMPLE 6

Effect of Persulfate on ECL Intensity

At first enough EE chips were manufactured with the procedure of Example 2. When studying the effect of various additives on the electrochemiluminescence, it was noticed that addition of persulfate increased the electroluminescence. This in all probability means that the persulfate was reduced in the process to produce sulfate radical. Sulfate radicals are known to produce chemiluminescence from Tb(III) ions and chelates in aqueous solution (S. Kulmala et al., Anal. Chim. Acta 294 (1994) 13-25.).

Figure 4:
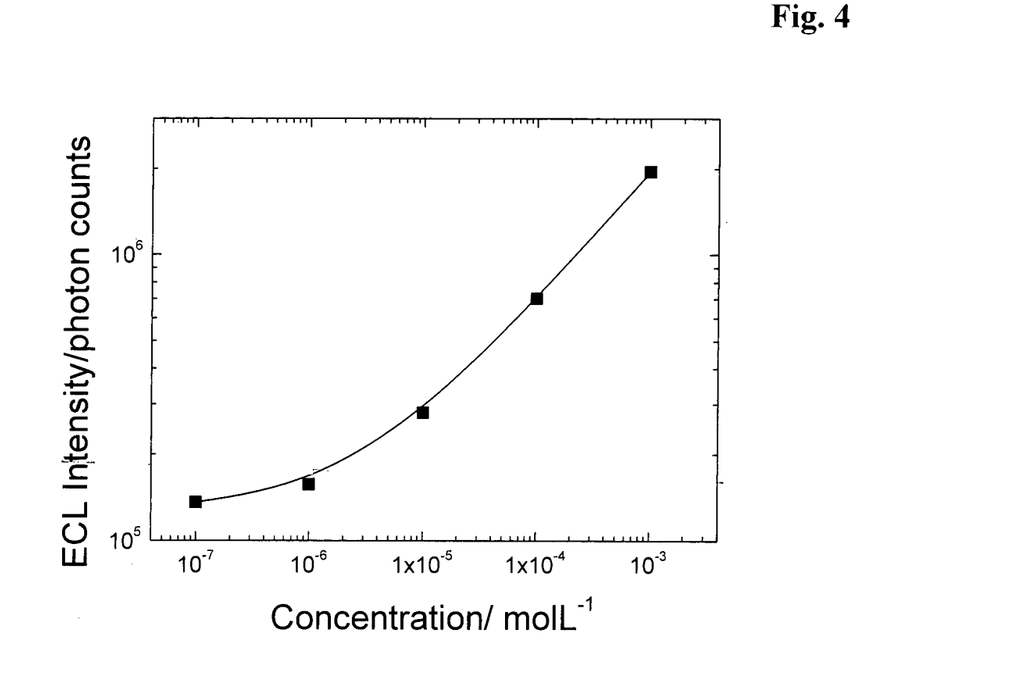
FIG. 4. Effect of persulfate on the intensity of electrochemiluminescence.

When the effect of potassium persulfate concentration on signal intensity was further studied it was noticed that increasing the persulfate concentration appeared to strongly enhance the ECL intensity of the Tb(III) chelate ($1\times10^{-6}$ M Tb-2,6-bis[N,N-bis(carboxymethyl)aminomethyl]-4-benzoylphenol) throughout the studied concentration range (FIG. 4).

It is probable that the increase of the intensity continues up to the highest dissolving amount of potassium persulfate (about 50 mM), and even higher concentrations can be reached with sodium persulfate. The measurement parameters were the same as in Example 2.

EXAMPLE 7

Effect of Acid and Base Treatments

When the stability of the electrodes was studied under acidic conditions and under basic conditions, it was found that the performance was better if the electrodes were used a second time. Because of this finding a comparison was made, in which EE chips manufactured by the process described in Example 2 were incubated for 15 minutes in 1M NaOH solution, 1M $H_2SO_4$ solution, or in 1M HCl solution. After the incubation the electrodes were washed with distilled water and measurements were made using 1 μM Tb-2,6-bis[N,N-bis(carboxymethyl)aminomethyl]-4-benzoylphenol chelate. The measurement parameters were the same as in Example 2. The results are given in the table below, and both the acid treatment and the basic treatment clearly increased the efficiency of the electrodes.

| 1 μM Tb(III) chelate | ECL intensity/photons | | | |
| --- | --- | --- | --- | --- |
| | untreated | 1M NaOH treatment | 1M $H_2SO_4$ treatment | 1M HCl treatment |
| Measurement | 337532 | 956184 | 697300 | 538215 |
| Repeated measurement | 317307 | 921739 | 615300 | 481643 |

EXAMPLE 8

Immunoassay with EE Chips Formed into a Whole Cell with PDMS Chip

PDMS chip was manufactured by moulding from Sylgard 184 silicon elastomer (curing agent 1:10) using a form on a Petri dish. The wet PDMS was degassed under vacuum and cured at 50° C. for 2 hours. The solidified PDMS was separated from the form and cut to pieces.

Figure 5:
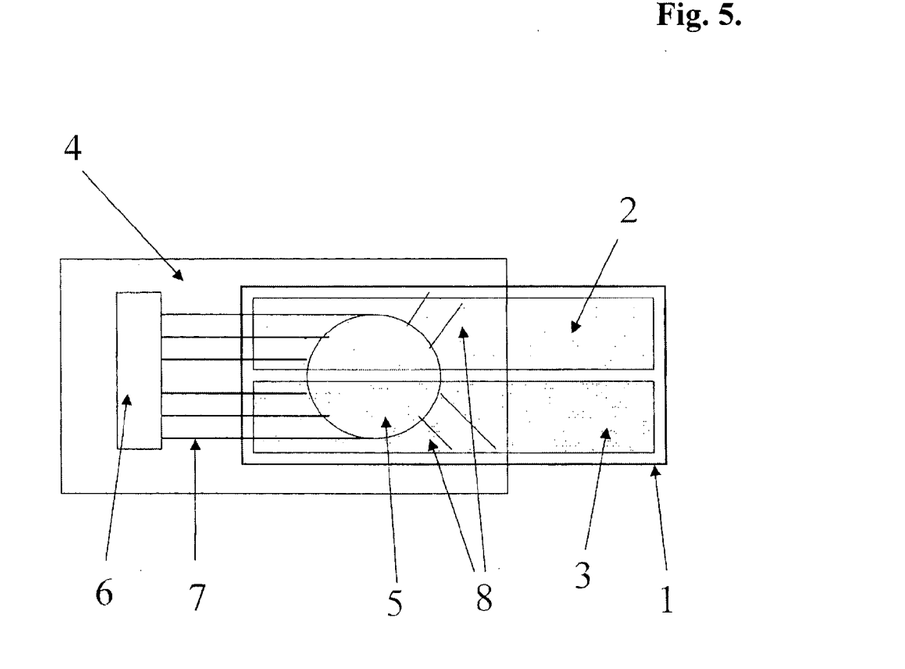

The PDMS chips had a sample and reagents feeding chamber at the left edge (Part 6 in FIG. 5) where the reagents needed for bioaffinity assay were dried before the analysis. This sample input chamber had been attached via microchannels (Part 7 in FIG. 5) to a combined incubation and measurement chamber (Part 5 in FIG. 5). Capillary forces and hydrostatic pressure moved the liquid to the incubation/measurement chamber while the air exited from the chamber via microchannels (Part 8 in FIG. 5). The incubation/measurement chamber had miniature pillars to keep the PDMS chip chamber at a constant size and to prevent it from compressing. The height of the incubation/measurement chamber was 0.35 mm, the volume was ca. 15 μL and the total thickness of the PDMS chip was 5 mm.

At first the top surface of glass chips (19.0 mm×10.0 mm) were plasma treated briefly. Then, a ca. 0.3 mm thick aluminium layer was vacuum deposited through a mask on the glass chips attached below the mask; both of the chip's electrodes (2 and 3 in FIG. 1) were formed. After this the aluminium electrodes were comprehensively coated with carbon paste (Creative Materials 110-04 Carbon Ink, Tyngsboro, Mass., USA) so that the contact areas of spring-loaded pins (to the pulse generator) at the right edge of the strip were left unpainted.

Human TSH was used as the model analyte. α-subunit attaching anti-TSH (MOAB, lot: M-21310, catalogue number MIT0406, conc. 6.87 mg/mL; Medix Inc, USA) was used as the primary (capturing) antibody, and the secondary (labeled) antibody was β-subunit specific anti-TSH (clone 5404, lot SPC099, conc. 5.5 mg/mL, Medix Biochemica Oy Ab, Finland). Calibration standards of hTSH were made by dilution from Wallac's concentrated stock solution (DELFIA hTSH kit, 324 mIU/mL TSH).

The labeled secondary antibody (anti-hTSH, clone 5404, 5.5 mg/mL, Medix Biochemica Oy Ab) was made by letting the isothiocyanate derivative of Tb chelate (Tb-2,6-bis[N,N-bis(carboxymethyl)aminomethyl]-4-bentsoylphenol chelate) react in 80 times molar excess with the antibody. The reaction was left to proceed overnight at pH 9.5. The labeled antibody was separated in a column which was 1 cm in diameter and had 5.5 cm Sephadex G-50 on top of 52 cm Sepharose 6B.

Once the carbon paste had dried, the electrodes were coated with the antibody in the well formed by the tape at the measuring cell area on the EE chip according to the following procedure:

150 μL of the solution containing 30 μg/mL of the capturing antibody (0.1M MES, 0.2 M borate, 0.025% bovine gammaglobuline pH 6.5) was added to the incubation well and incubated for 3 hours in closed plastic boxes with azide-containing water at the bottom beneath stands. After the coating the cell area was washed with a washing solution (0.05M Tris-$H_2SO_4$ buffer, pH 7.75, 0.1% bovine albumin, 0.1% Tween 20, and 0.1% $NaN_3$).

Next a PDMS chip (25 mm×14 mm, 5 mm thick; Part 4 in FIG. 5) was attached to the EE chip with clamps so that the chips pressed suitably tightly against each other. After this, 20 μL of the solution was added to the sample inlet chamber (Part 6 in FIG. 5) located at the left edge of the PDMS-EE cassette. The solution contained 100 ng of the labeled secondary antibody in 0.05 M Tris-$H_2SO_4$ buffer (pH 7.75, 0.1% bovine albumin, 0.1% Tween 20, and 0.1% $NaN_3$).

0.2 M sodium tetraborate buffer (pH set to 7.8 with $H_2SO_4$; 0.5% bovine albumin, 0.05% bovine gammaglobulin, 0.01% Tween 20, and 0.1% $NaN_3$) was used as the immunoassay and measurement buffer. At first 25 μL of hTSH standard was added to 175 μL of immunoassay/measurement buffer. The mixture was pipetted to the sample inlet chamber (Part 6, FIG. 5), where the label was already in dried form. The sample dissolved the label and the mixture moved by capillary forces and hydrostatic pressure to the incubation/measurement chamber (Part 5, FIG. 5) via microchannels (Part 7, FIG. 5) while air exited from the cell via other microchannels (Part 8, FIG. 5).

Figure 6:
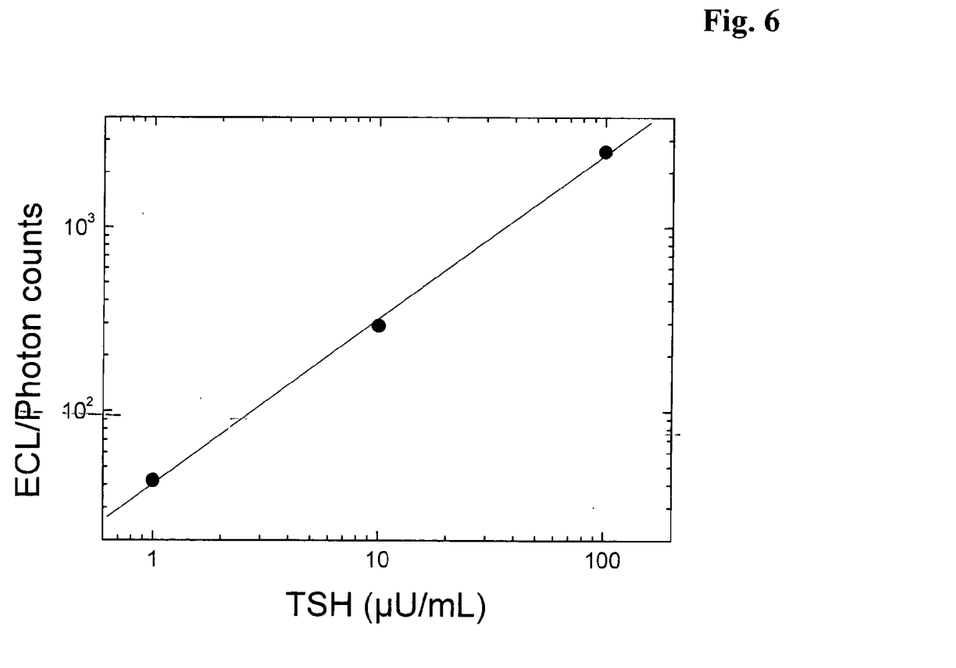
FIG. 6. Immunoassay in a cassette formed of an EE chip and a PDMS chip.

After 15 minutes of incubation the ECL intensity was measured from each PDMS-EE cassette using a measurement apparatus consisting of a laboratory-made coulostatic pulse generator, a Stanford Research Instruments SR400 photon counter, a Nucleus MCS-II multichannel card and a closed cell measurement space made of black plastic and with a Perkin Elmer channel photomultiplier tube module (pulse amplitude −45V, pulse charge 15 μC/pulse, pulse frequency 20 Hz; ECL intensity was integrated over 200 excitation cycles with delay time 0.05 ms and measuring window 6.0 ms). The results of the measurement are shown in FIG. 6.

EXAMPLE 9

Hybridization Assay on EE Chips

EE chips were manufactured of vaporised aluminium and carbon paste in the same way as in Example 6. The cell area of the chips was formed with tape in the same way as in Example 1.

The sequence to be determined was a 120 nucleotide fragment that is common to human entero- and rhinoviruses. The fragment had been copied with RT-PCR (Lönnrot et al., J. Med. Vir. 56 (1999) 378-84.). This sequence is in routine use in centralized diagnostic laboratories to determine entero- and rhinoviruses.

The probe 1 (TTA-GCC-GCA-TTC-AGG-GGG-CGA-AAA-AA-$C_6$—$NH_2$ (SEQ ID NO:1), MedProbe AB, Sweden), which was complementary to the 5' end of the sequence to be determined, was coated on carbon paste electrodes. For the coating, (APTES) amino groups were added through silanization with (3-aminopropyl)triethoxysilane on electrodes covered with an oxide layer. A poly-A tail, a six-carbon aliphatic carbon chain and an ending amino group were added to the 3' end of probe 1. The final covalent bonding was done with DSS double reagent (disuccinimidyl suberate) according to the instructions of the producer.

The second probe "Probe 2" (($NH_2$)$_4$-GA-AAC-ACG-GAC-ACC-CAA-AGT-A) (SEQ ID NO:2)) was labeled with the isothiocyanate derivative of Tb-chelate (Tb-2,6-bis[N,N-bis(carboxymethyl)aminomethyl]-4-bentsoylphenol chelate) by incubating the probe 80 times excess chelate in 0.5 M sodium carbonate buffer (pH9.5) overnight. After the incubation the labeled probe was cleaned with a Sephadex G50 column (NAP-5 column, GE Healthcare).

Figure 7:
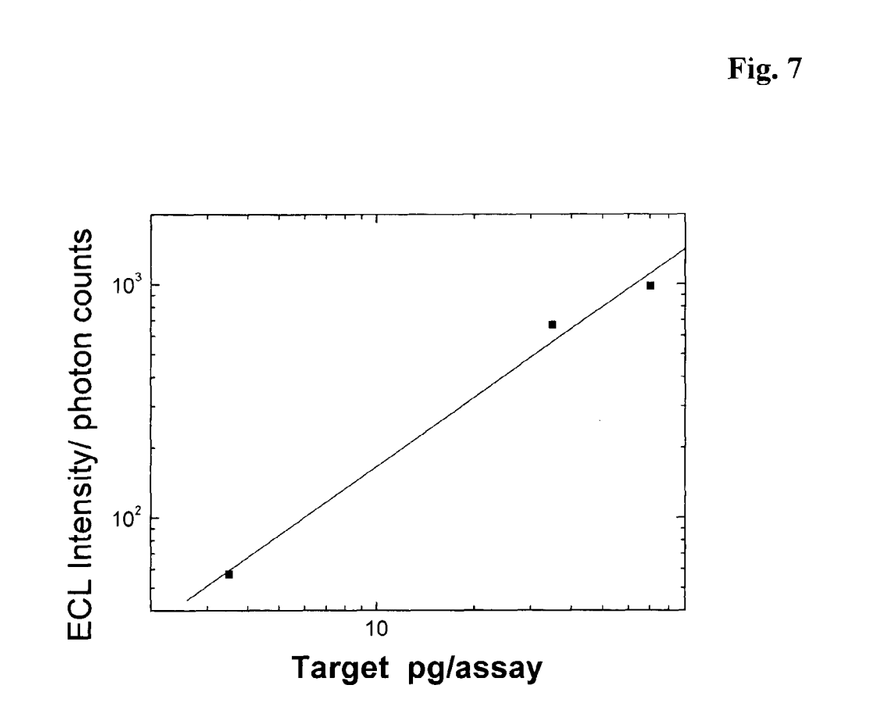
FIG. 7. Hybridization assay on an EE chip.

The hybridization was performed by the following means. The RT-PCR multiplied DNA sample (20 μL, dilutions 1:50, 1:100 and 1:1000) was denatured by addition of 180 μL NaOH (50 mmol/L) and incubated at 37° C. for 5 min. The samples were then neutralized by addition of 200 μL neutralization buffer (6×SSC, 0.3% Tween 20, 20 mmol/L citric acid). 10 μL of both the neutralized sample and the labeled probe 2 (0.6 ng/4, 50 mmol/L Tris-HCl buffer pH 7.8, 600 mmol/L NaCl, 1% Triton X 100 and 1% Blocking reagent (Roche)) were transferred to a new test tube. After mixing, 3.5 μL of the mixture was pipetted on the membrane part of the test strip. After hybridization (5 min) the membrane was removed from the silicon electrode, the EE chip was washed 3 times and ECL was measured. The graph of the sample dilutions is shown in FIG. 7. The measurement parameters were the same as in Example 8.

EXAMPLE 10

Simultaneous Determination of Two Immunoanalytes on One EE Chip

C-reactive protein (CRP) and thyroid stimulating hormone (TSH) were determined simultaneously so that one of the electrodes was coated with a CRP capturing antibody and the other with a TSH capturing one.

The electrodes of the EE chip were coated with the capturing antibody in rectangle-shaped wells made of tape. The rectangular holes were made in the tape with a scalpel using a template. Each of the wells covered a slightly larger area of the corresponding electrode than the final, round cell area, which was at the end of the pretreatment manufactured by adding another tape with a round hole, as in FIG. 1.

Both of the antibodies were simultaneously coated on the electrode, each in its own tape wells. Anti-TSH (anti-hTSH, MIT0406, Medix Biotech Inc., USA) was coated on the electrode by incubating the antibody (25 µg/mL, 150 µL) for 2 hours at room temperature in a solution containing 0.1 M MES, 0.03M $H_3BO_3$, 0.5 mM potassium citrate, 0.025% glutaraldehyde, and 0.05% bovine gammaglobuline. After the incubation the tape well was washed 3 times with a washing solution (50 mM Tris-HCl buffer pH 7.8 with 0.9% NaCl, 0.09% $NaN_3$ and 0.05% Tween 20). After the washing the coated electrode was saturated by incubating a saturation solution (50 mM Tris-HCl pH 7.8 with 0.05% $NaN_3$, 0.9% NaCl, 0.1% BSA and 6% D-sorbitol) in the tape well for 30 min. After the saturation the tape well was removed (simultaneously with the one from the anti-CRP coating) from the electrode area and the EE chip was dried at 30° C. for 2.5 h.

In an analogous manner, anti-CRP was coated by incubating (in the tape well on the other electrode) the antibody (20 µg/mL, 150 µL) for 2 hours at room temperature with 50 mM Tris-HCl buffer (pH 7.8 with 0.05% $NaN_3$ and 0.9% NaCl). After the incubation the tape well was washed 3 times with washing solution (50 mM Tris-HCl buffer pH 7.8 with 0.9% NaCl, 0.09% $NaN_3$ and 0.05% Tween 20). After washing the coated electrode was saturated by incubating a saturation solution (50 mM Tris-HCl pH 7.8 with 0.05% $NaN_3$, 0.9% NaCl, 0.1% BSA and 6% D-sorbitol and 1 mM $CaCl_2$) in the tape well for 30 min. After the saturation the tape well was removed (simultaneously with the one from the anti-TSH coating step) from the electrode area and the EE chip was dried at 30° C. for 2.5 h.

Labeled antibodies were dried in the membrane in the following manner. Anti-hCRP antibody (74 µg/mL, Medix Biochemica Oy Ab anti-hCRP clone 6404) labeled with Tb(III) chelate (Tb-2,6-bis[N,N-bis(carboxymethyl)aminomethyl]-4-benzoylphenol) and anti-hTSH antibody (80 µg/mL, clone 5404, Medix Biochemica Oy Ab) labeled with the same Tb(III) chelate were dissolved in 50 mM Tris-HCl buffer (pH 7.7, 0.05% $NaN_3$, 0.9% NaCl, 0.5% BSA, 0.05% bovine gammaglobulin, 0.01% Tween 20, 1 mM $CaCl_2*H_2O$). 0.5 µL of the antibody-buffer solution was pipetted in the middle of a membrane (10×10 mm, Nuclepore Membrane 112110, Whatman) and dried overnight at room temperature and room air.

The hCRP standard samples needed in immunoassays (CRP content 1, 10 and 100 ng/mL) were made in test tubes by diluting the CRP standard solution (Scripps, cat.no.00124) with 50 mM Tris-HCl buffer (pH 7.7, 0.05% $NaN_3$, 0.9% NaCl, 0.5% BSA, 1 mM $CaCl_2*H_2O$). Analogously the TSH standard samples (1, 10 and 100 mIU/mL) were made by diluting the TSH standard (324 mIU/mL, Wallac, DELFIA hTSH kit) with 50 mM Tris-HCl buffer (pH 7.7, 0.05% $NaN_3$, 0.9% NaCl).

Figure 8:
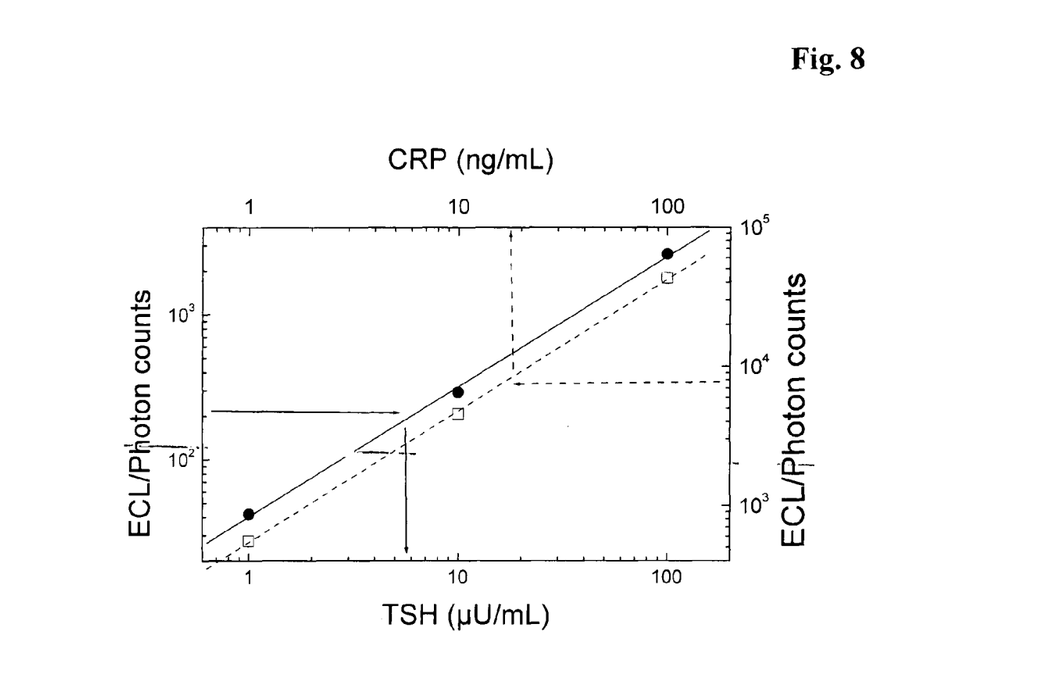
FIG. 8. Two simultaneous immunoassays on an EE chip.

The immunoassay was performed so that both the EE chip and the porous membrane were dry in the beginning. The membrane was applied exactly on top of the tape-well defined cell area of the EE chip and locked in place with tape from the other end. The immunoassay was begun by adding both analyte standards 3.5 µL in the middle of the porous membrane (CRP 0 ng/mL and TSH 0 mIU/mL; CRP 1 ng/mL and TSH 1 mIU/mL; CRP 10 ng/mL and TSH 10 mIU/mL; CRP 100 ng/mL and TSH 100 mIU/mL). After incubating 10 min at room temperature the membrane was removed, the cell area of the EE chip was washed with the measurement buffer and 80 µL of the measurement buffer (0.05 M $Na_2B_4O_7$ and $2 \times 10^{-4}$ M $K_2S_2O_8$) was added. Both analytes were measured so that first 10 excitation cycles were measured with the anti-TSH electrode as the cathode, then the polarity was changed for another 10 cycles with anti-CRP electrode as the cathode. The measurement was repeated 5 times and signals from both electrodes were summed together. From the results it would appear that light is primarily produced at the cathode, because the TSH response was received from the left electrode, and such a double assay would seem to work, although it may not necessarily be sensible to measure these particular compounds, TSH and CRP, in the same sample. The measurement results have been presented in FIG. 8 and the parameters were the same as in Example 8.

The invention claimed is:

1. A method to electrically excite lanthanide-chelates in electrolyte solutions, wherein excitation is performed with voltage pulses with duration between 1 ns and 1000 s and frequency between 0.001 Hz-1200 MHz and amplitude between 1V-400V, in an electrochemical cell consisting of two electrodes, said electrodes being carbon paste electrodes, both of which can be used alternately as an anode or a cathode, and wherein the lanthanide-chelate is excited on cathode-electrode.

2. The method according to claim 1, wherein polarity of the electrodes is changed at least once during a measurement, as a result of which both electrodes will have functioned as an anode and as a cathode during the measurement.

3. The method according to claim 1, wherein consecutive excitation pulses are bipolar, as a result of which the electrodes function during the pulses by turns as anodes and as cathodes.

4. The method according to claim 1, wherein the carbon paste electrodes are printed, sprayed or painted.

5. The method according to claim 1, wherein the carbon paste electrodes are on top of another conductor, said conductor comprising surface of metal film, conductive ink or conductive polymer.

6. The method of claim 1, wherein the lanthanide-chelate is Tb(III)-chelate.

7. The method of claim 1, wherein the lanthanide chelate is a detection label attached to a biological molecule in a bioassay.

* * * * *